United States Patent [19]
Chihara et al.

[11] Patent Number: 5,273,045
[45] Date of Patent: Dec. 28, 1993

[54] ULTRASONIC EQUIPMENT AND ITS CATHETER-TYPE ULTRASONIC PROBE

[75] Inventors: Kunihiro Chihara, Hirakata; Hiroshi Ishikawa, Kawasaki; Kazuhiro Watanabe, Kawasaki; Kenji Kawabe, Kawasaki; Takaki Shimura, Kawasaki, all of Japan

[73] Assignee: Fujitsu Limited, Kawasaki, Japan

[21] Appl. No.: 886,816

[22] Filed: May 22, 1992

[30] Foreign Application Priority Data

May 23, 1991 [JP] Japan .................................. 3-118872

[51] Int. Cl.⁵ .............................................. A61B 8/12
[52] U.S. Cl. .......................... 128/662.06; 128/661.01; 128/772
[58] Field of Search ................... 128/661.01, 662.06, 128/91.6, 772, 662.03

[56] References Cited

U.S. PATENT DOCUMENTS

| | | | |
|---|---|---|---|
| 4,327,738 | 5/1982 | Green et al. | 128/662.06 |
| 4,576,177 | 3/1986 | Webster, Jr. | 128/660.03 |
| 4,951,677 | 8/1990 | Crowley et al. | 128/662.06 |
| 5,081,993 | 1/1992 | Kitney et al. | 128/916 |
| 5,174,296 | 12/1992 | Watanabe et al. | 128/662.03 |

*Primary Examiner*—William E. Kamm
*Assistant Examiner*—George Manuel
*Attorney, Agent, or Firm*—Staas & Halsey

[57] ABSTRACT

An Ultrasonic Equipment and its Catheter-type Ultrasonic Probe can be inserted in capillaries such as blood vessels, and comprises a catheter-type ultrasonic probe for generating ultrasonic waves by a piezoelectric transducer arrayed at its tip. A plurality of the piezoelectric transducer segments are arrayed on a two-dimensional plane, perpendicular or approximately perpendicular to the insertion direction of the probe into a capillary with their ultrasonic wave emitting surface faced in the insertion direction. A part of the plane is cut out to provide a guide unit for passing a treating catheter or a guide wire in the insertion direction.

8 Claims, 9 Drawing Sheets

ULTRASONIC EQUIPMENT AND ITS CATHETER-TYPE ULTRASONIC PROBE

BACKGROUND OF THE INVENTION

The present invention relates to a catheter-type ultrasonic probe capable of searching in capillaries, that is, fine hollow tubes, such as blood vessels for use mainly in medical diagnosis and treatment, and to an ultrasonic equipment provided with the above described probe. This ultrasonic equipment can recognize through a three-dimensional image the state of the inner side of a blood vessel and the existence of atheroma, etc.

Conventionally, when blood vessels are diagnosed through ultrasonic waves, an ultrasonic probe 101 is inserted in a blood vessel T as shown in FIG. 1 to have ultrasonic beams 103 generated by a piezoelectric transducer 102 rotatively scan each part of an object by mechanically revolving the piezoelectric transducer 102 in the direction indicated by the arrow B. The transducer is provided at the tip of the ultrasonic probe 101 and generates ultrasonic beams in the perpendicular direction to the insertion direction A. Then, according to the reflected wave from each part of the blood vessel T, the inner surface of the cross-section of the blood vessel T perpendicular to the insertion direction A is displayed in a two-dimensional image.

In another operation, an ultrasonic probe 201 shown in FIG. 2 has ultrasonic beams 203 rotatively scan each part of an object by mechanically rotating in the direction indicated by the arrow B a reflector 204 having a reflecting surface set at about 45 degrees to the insertion direction A while the reflector 204 reflects the ultrasonic beam 203 generated by a piezoelectric transducer 202 and emitted in the opposite direction to the insertion direction A.

In a different operation, an ultrasonic probe 301 shown in FIG. 3 has ultrasonic beams 303 rotatively and electrically scan each part of an object by sequentially driving in the direction indicated by the arrow B a plurality of piezoelectric transducer segments 302 arrayed around the circumference of the tip of the probe.

The above described ultrasonic diagnotic techniques are performed to recognize the state of an object to be diagnosed or treated or of an object medically treated with the aid of a two-dimensional image. In a medical treatment, the ultrasonic probe is pulled out of the blood vessel after the part of an object to be treated is determined. Then, a catheter for applying medicines or a catheter provided with a cutter for removing atheroma is inserted to the target part in the blood vessel.

The conventional ultrasonic probes 101, 201, and 301 shown in FIGS. 1-3 perform medical diagnoses according to the two-dimensional images of views perpendicular to the insertion direction A. Therefore, the diagnoses are limited to the inner surface of one cross-section of a blood vessel. Besides, the two-dimensional image indicates either the inner surface of a cross-section enclosing the piezoelectric transducer segments 102 and 302 (FIGS. 1 and 3), or the inner surface of a cross-section enclosing the point behind the piezoelectric transducer segment 202 (FIG. 2) in the insertion direction A. As described above, in an actual medical treatment, a treating catheter, etc. must be inserted to a target part in a blood vessel after the ultrasonic probe is pulled out of the blood vessel.

As described above, actual treatments cannot be performed while a target part of an object to be medically treated is monitored through conventional equipment.

SUMMARY OF THE INVENTION

An object of the present invention is to provide an ultrasonic probe and an ultrasonic equipment capable of obtaining a three-dimensional image of a part forward of the ultrasonic wave emitting surface of a piezoelectric transducer in the insertion direction of the ultrasonic probe, and of monitoring the target part through a three-dimensional image when actual medical treatment is performed using a treating catheter, etc.

An ultrasonic probe of the present invention is configured such that it can be inserted in a capillary and is provided at its tip with a piezoelectric transducer for generating ultrasonic waves. The features of the ultrasonic probe are described below. First, a plurality of the piezoelectric transducer segments are arrayed such that their ultrasonic wave emitting surfaces face in the insertion direction on a two-dimensional plane perpendicular or approximately perpendicular to the insertion direction into the capillary. Second, a part of the plane on which a plurality of piezoelectric transducer segments are arrayed is cut out not to be provided with piezoelectric transducer segments but to serve a guide unit for passing in the insertion direction a treating catheter or a guide wire. Thus, the probe of the present invention is formed of a catheter.

The ultrasonic equipment of the present invention is provided with the above described catheter-type ultrasonic probe. One of a plurality of the above described piezoelectric transducer segments forming the probe is used as an ultrasonic wave sending element, and all the other transducer segments are used as reflected wave receiving elements. An ultrasonic wave generated by the sending element and reflected at a measurement point is received by a plurality of the receiving elements, and a three-dimensional image is generated according to their signals.

A means for generating a three-dimensional image according to the signals of the above described receiving elements comprises, for example, an A/D converter for converting each of the output signals of a plurality of the receiving elements to a digital signal, a wave memory for storing according to each of the digital signals outputted by the A/D converter wave data indicating the transmission time in which an ultrasonic wave is generated by the sending element, reflected at the measurement point, and received by each of the receiving elements, an operating circuit for identifying a measurement point corresponding to each piece of wave data by comparing the wave data at each measurement point stored in the wave memory with a prepared data mask indicating the relationship between a measurement point and ultrasonic wave transmission time, and for generating three-dimensional image data according to the identification result, and a display unit for displaying three-dimensional image data obtained by the operating circuit.

The catheter probe of the present invention is provided with a plurality of piezoelectric transducer segments arrayed on a plane perpendicular to its insertion direction with their ultrasonic wave emitting surface faced in the insertion direction. Therefore, in the ultrasonic equipment of the present invention provided with the probe, the ultrasonic waves emitted by a piezoelectric transducer are reflected at a measurement point forward of the piezoelectric transducer in the insertion direction. The reflected waves are received by other piezoelectric transducer segments and processed as received signals. As a result, a three-dimensional image of a target part forward of the piezoelectric transducer segments in the insertion direction can be obtained.

The probe is also provided with a guide unit for passing a treating catheter or a guide wire in the insertion direction. Therefore, during a diagnosis, the probe can be inserted exactly into a target point to be diagnosed while each part forward of the ultrasonic wave emitting surfaces is monitored through a guide wire passing through the guide unit. Likewise, during a treatment, a treating catheter is inserted instead of the guide wire to correctly treat a target part to be medically treated while it is visually monitored.

DESCRIPTION OF THE PREFERRED EMBODIMENT

An embodiment of the present invention is explained below by referring to the corresponding drawings.

Figure 1:
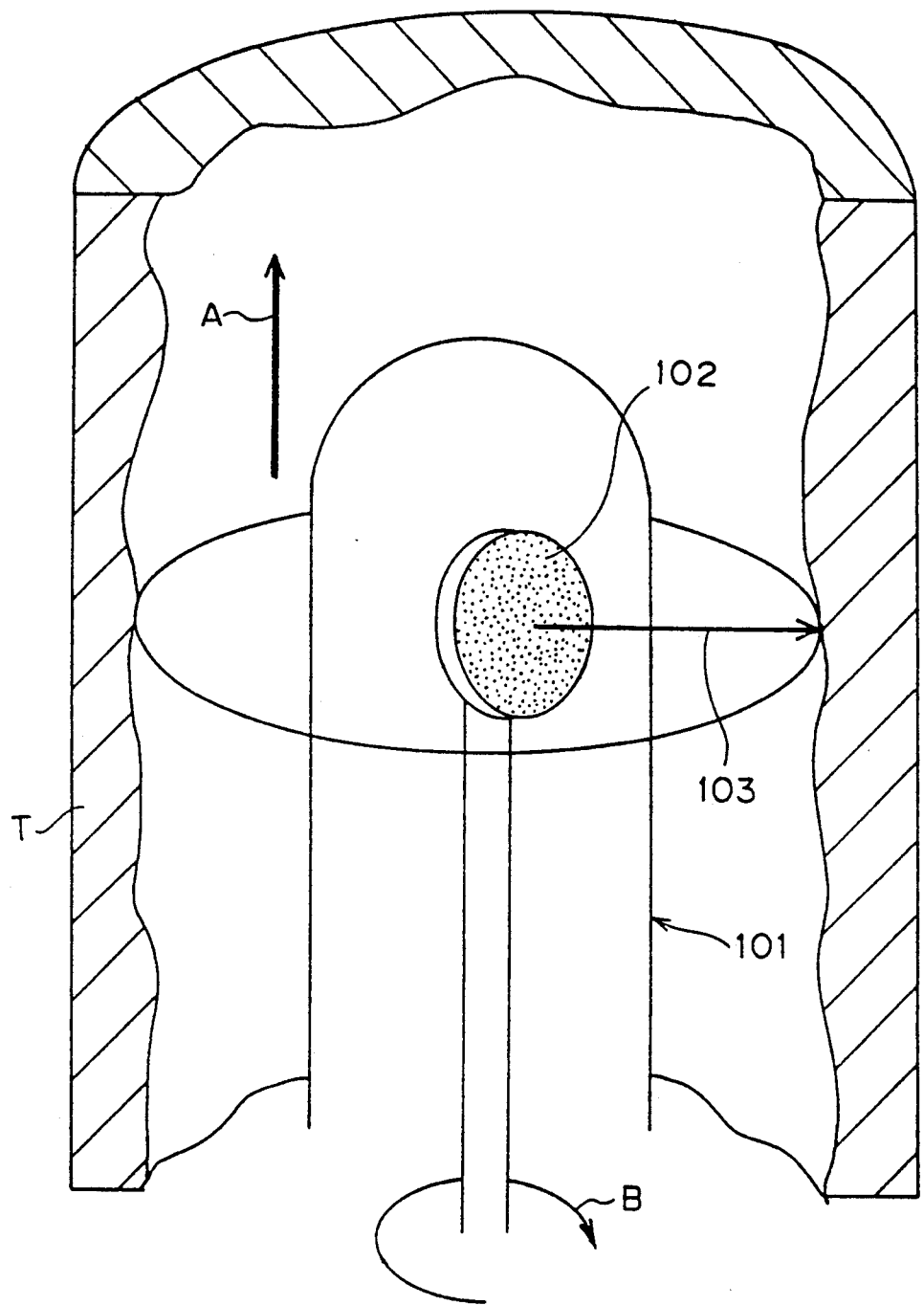
FIG. 1 is an oblique view illustrating the first example of a conventional ultrasonic probe.
Figure 2:
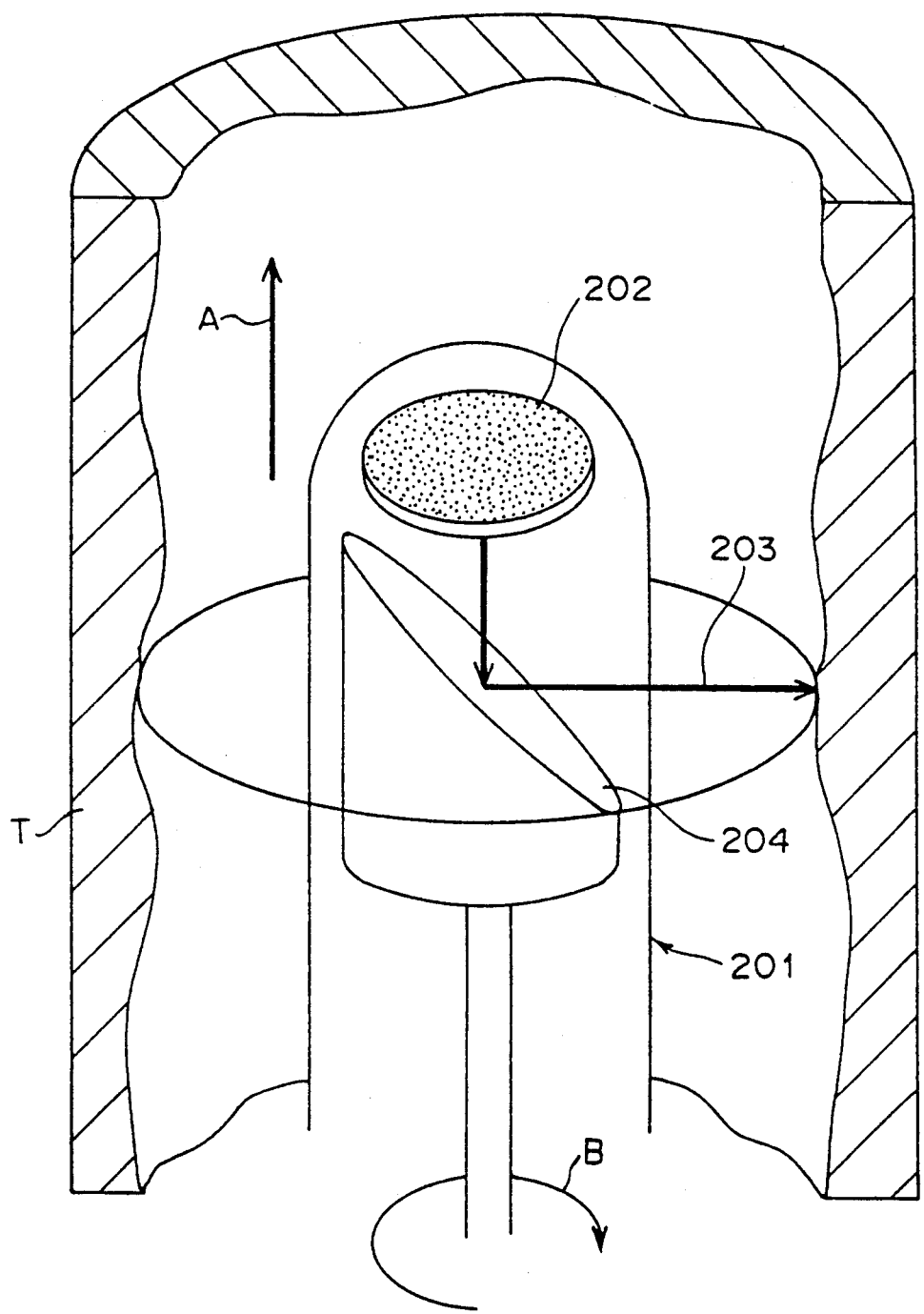
FIG. 2 is an oblique view illustrating the second example of a conventional ultrasonic probe.
Figure 3:
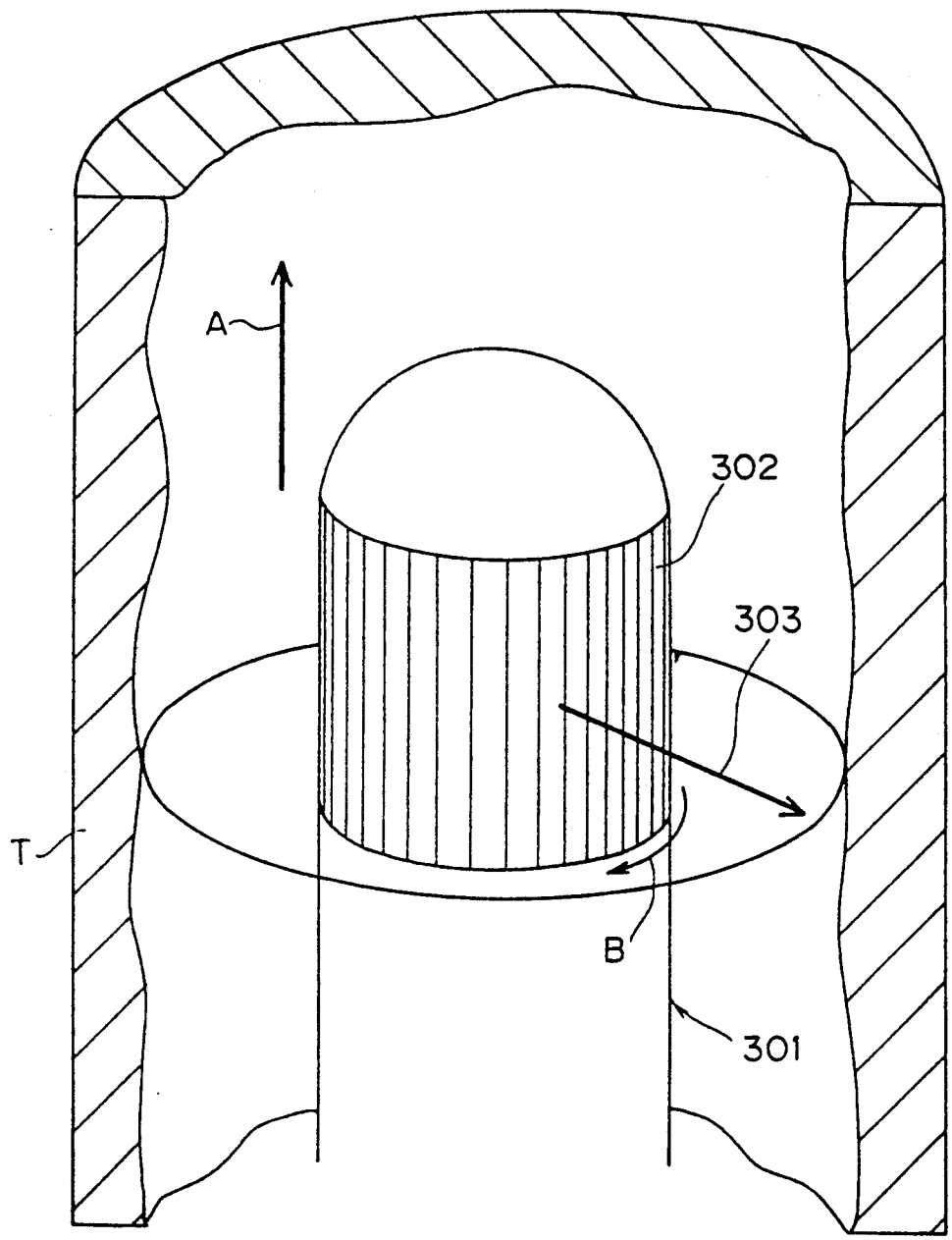
FIG. 3 is an oblique view illustrating the third example of a conventional ultrasonic probe.
Figure 4:
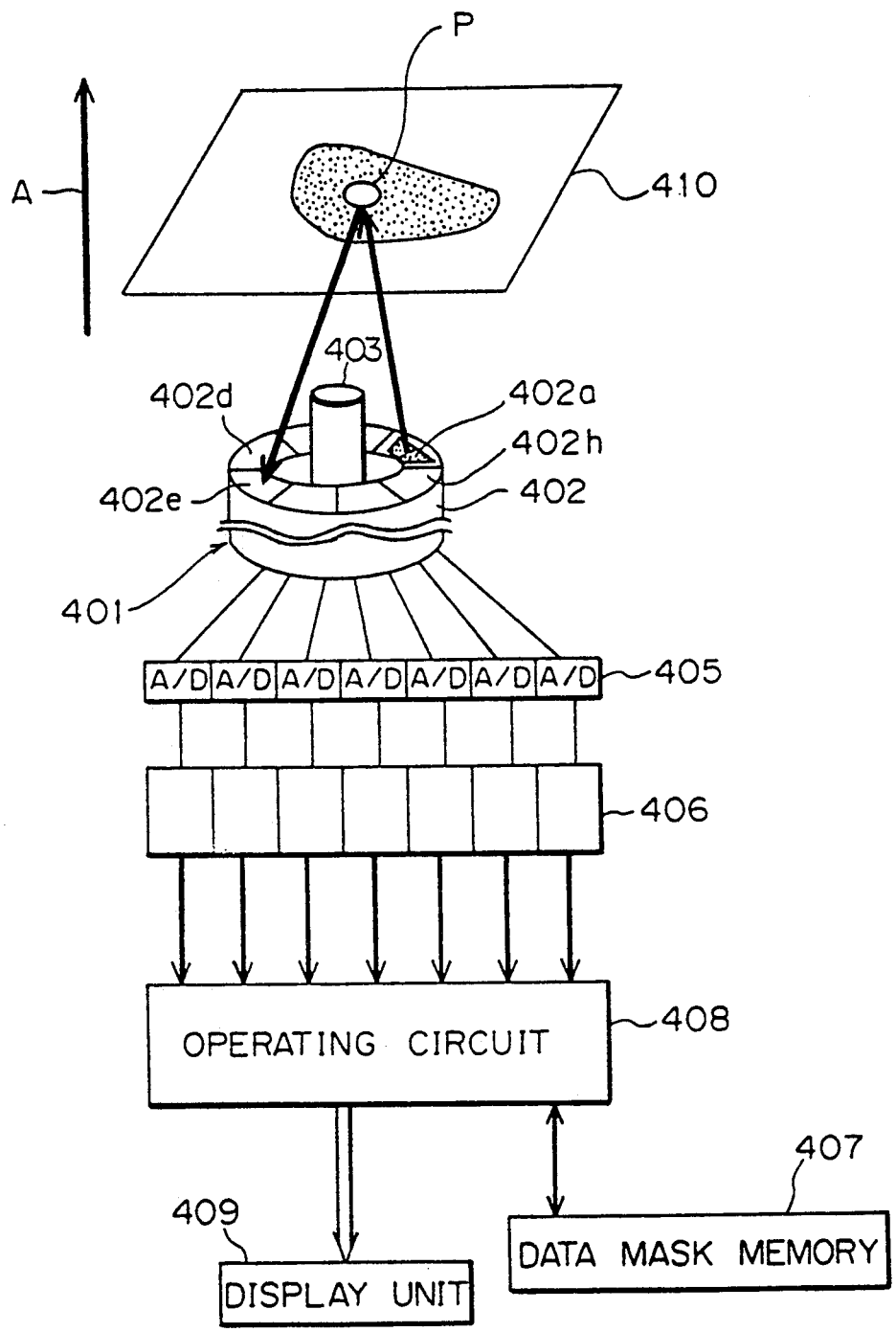
FIG. 4 shows the configuration of the ultrasonic equipment used in the first embodiment of the present invention.
Figure 5:
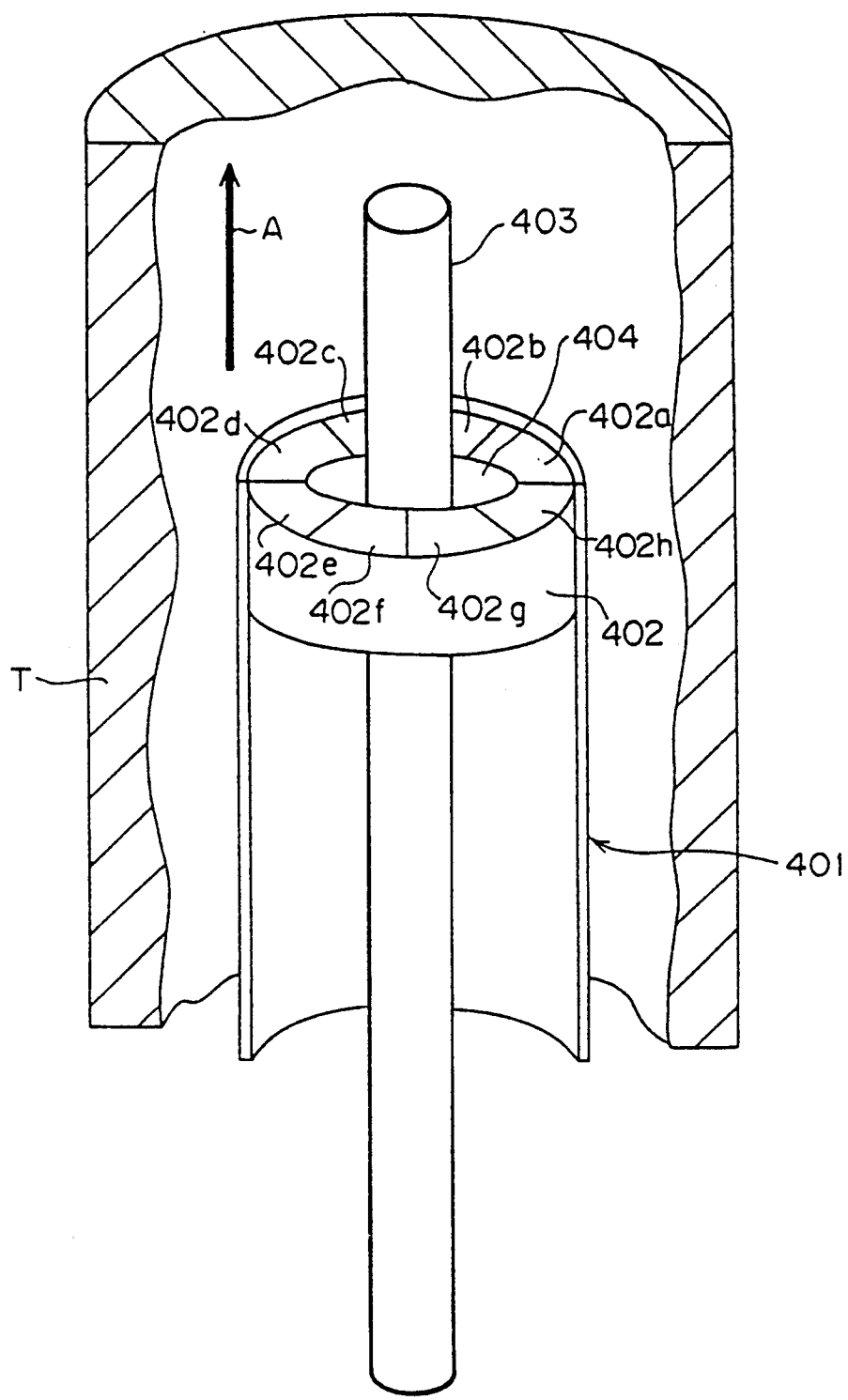
FIG. 5 is an oblique view illustrating the configuration of the ultrasonic probe used in the first embodiment of the present invention.

The ultrasonic equipment of the first embodiment of the present invention is provided with an ultrasonic probe 401 formed of a catheter capable of being inserted into a blood vessel in the direction indicated by the arrow A as shown in FIG. 4. At the tip of the probe 401, a plurality of piezoelectric transducer segments 402 (402a–402h) are arrayed on a two-dimensional plane perpendicular or approximately perpendicular to the insertion direction A as shown in FIG. 5. On each piezoelectric transducer on ultrasonic wave emitting surface faces in the insertion direction A. The piezoelectric transducer 402 comprises a plurality of piezoelectric transducer segments obtained by radially dividing a ring-shaped transducer (into eight segments in FIG. 5). The central space serves as a guide unit 404 for passing a guide wire 403 or a treating catheter. Among the eight equally divided piezoelectric transducer segments 402, one is used as an ultrasonic wave sending element 402a, and the others 402b–402h are used as reflected wave receiving elements.

The ultrasonic equipment shown in FIG. 4 comprises the catheter-type ultrasonic probe 401, a driver (not shown in the drawings) for generating an ultrasonic wave impulse by driving the sending element 402a, and a means for generating a three-dimensional image according to received signals obtained by receiving reflected waves of ultrasonic waves at each of the receiving elements 402b–402h. The three-dimensional image generator comprises seven A/D converters 405 for converting each of the output signals of the receiving elements 402b–402h to a digital signal, a wave memory 406 for storing according to each of the digital signals outputted by the A/D converters wave data indicating the transmission time in which an ultrasonic wave is generated by the sending element 402a, reflected at the measurement point P, and received by each of the receiving elements 402b–402h, a data mask memory 407 for storing a predetermined data mask indicating the relationship between a measurement point and ultrasonic wave transmission time, an operating circuit 408 for identifying a measurement point corresponding to each piece of wave data by comparing the wave data at each measurement point stored in the wave memory 406 with the data mask stored in the data mask memory 407, and for generating three-dimensional image data according to the identification result, and a display unit 409 for displaying three-dimensional image data obtained by the operating circuit 408.

Figure 6:
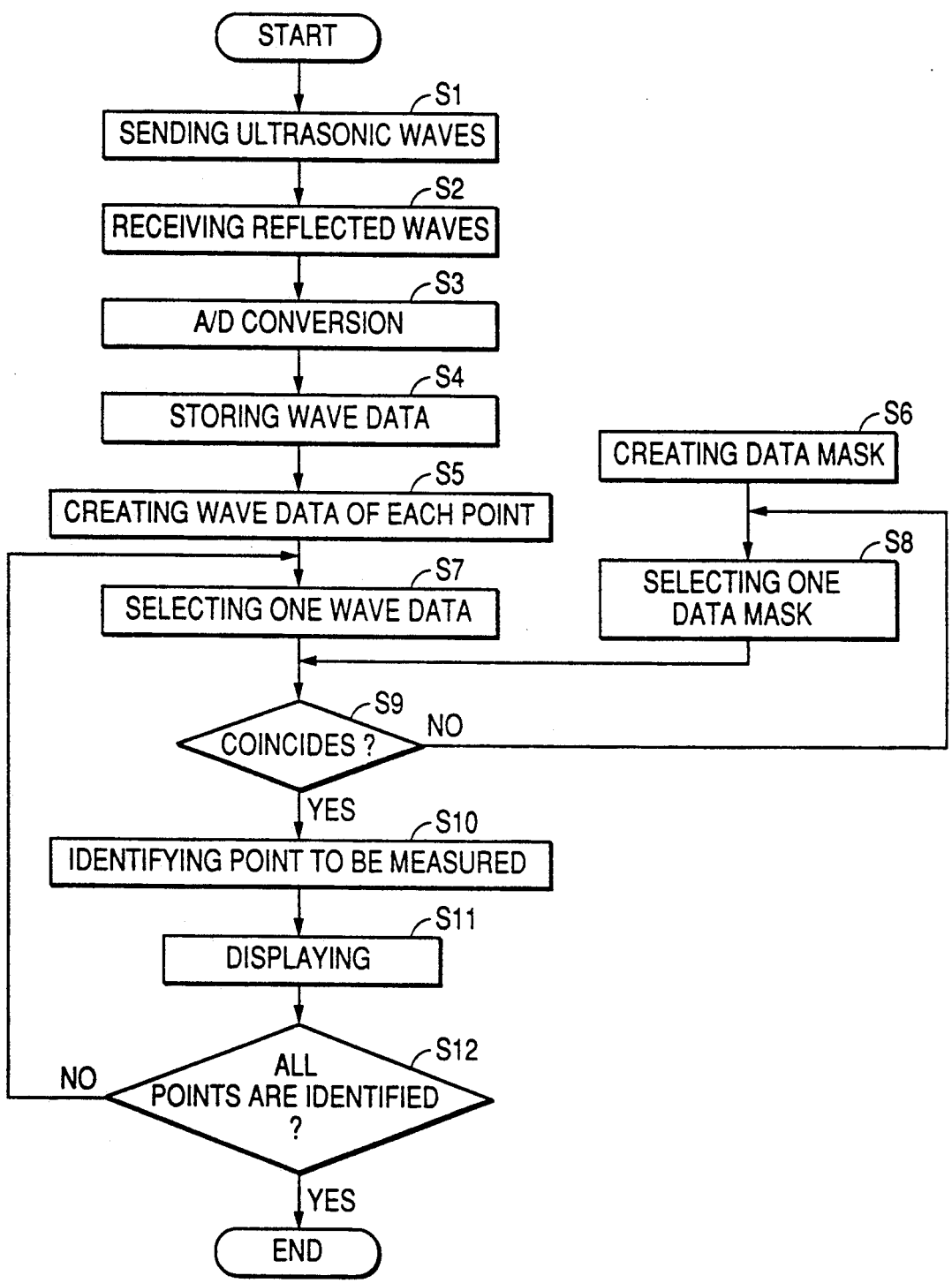
FIG. 6 is a flowchart for explaining the operation of the ultrasonic equipment used in the first embodiment of the present invention.

Next, the actual operation of the ultrasonic equipment with the above described configuration is explained below by referring to FIG. 6. In the explanation, the ultrasonic probe 401 is inserted in a blood vessel T so that the state of the blood vessel can be diagnosed ultrasonically.

Sending element 402a is driven by the above described driver, and an ultrasonic wave impulse (spherical wave) is sent forward in the insertion direction A therefrom (S1). Since the ultrasonic wave returns after being reflected at a measurement point P, it is received by the other seven receiving elements 402b–402h (S2). Then, an analog signal (received signal) outputted by the receiving elements 402b–402h is converted to a digital signal by the A/D converter 405 (S3). The digital signal provides the transmission time in which an ultrasonic wave generated by sending element 402a travels via the measurement point P and is received by each of the receiving elements 402b–402h. Accordingly, data are stored in an address area corresponding to the above described transmission time within the storage area corresponding to each of the receiving elements 402b–402h in the wave memory 406 when a digital signal is given by each of the A/D converters 405 corresponding to each of the receiving elements 402b–402h. Then, all data relating to one measurement point P are stored as one piece of wave data (S4). Likewise, each piece of wave data can be generated for each of a number of measurement points (S5).

Next, the operating circuit 408 generates three-dimensional image data according to the above described wave data. Before this, a data mask must be prepared experimentally or by a calculation (S6). A data mask comprises data indicating the relationship between a measurement point and the transmission time in which an ultrasonic wave is transmitted by way of the measurement point. To prepare a data mask, every point to each depth of an object to be measured (a blood vessel, for example) must be selected as a point to be measured (reflecting object). Then, the transmission time in which an ultrasonic wave is transmitted through the measurement point is calculated on condition that an ultrasonic wave is transmitted with the same positional relationship between the actual sending element 401a and receiving elements 402b–402h. Then, data are stored in an address area corresponding to the above described transmission time within the storage area corresponding to each of the receiving elements in the data mask memory 407. Then, all data relating to one measurement point are stored as one piece of data mask. Likewise, each piece of data mask can be generated for each of a number of measurement points.

Then, the operating circuit 408 selects one piece of wave data from the above described wave memory 406 (S7), and simultaneously selects one data mask from the above described data mask memory 407 (S8). The selected data are compared and it is determined whether or not they coincide with each other (S9). If not, a data mask is sequentially selected from the data mask memory 407 until a coincident result is obtained (S8). At each selection, the comparison (S9) is made. "Coincidence" means that a specific measurement point corresponding to the coincident data mask coincides with an unknown measurement point P corresponding to the wave data obtained by an actual measurement. Therefore, the unknown measurement point P is identified as the specific measurement point (S10). Thus, the identified measurement point P is displayed on the display unit 409 as a point in three-dimensional image data (S11). The above described processes S7–S11 are performed repeatedly until all measurement points are identified (S12).

Thus, a three-dimensional image data of an object to be measured can be obtained. A three-dimensional image can also be obtained by generating and combining a plurality of C mode images 410 (FIG. 4) for each depth after an object to be measured is cut to make a cross-section horizontal to the ultrasonic wave emitting surface of the piezoelectric transducer 402. The three-dimensional image is displayed by a voxel representation. Then, the three-dimensional representation can be realized by displaying an image with variations in gradation code and pixel size. For example, a point near the surface is displayed thick and big, while a point at a deep level is displayed thin and small.

Therefore, the embodiment easily generates a three-dimensional image of a part to be medically treated forward of the piezoelectric transducer 402 in the insertion direction A of the probe 401. Furthermore, the probe 401 comprises the guide unit 404 for passing in the insertion direction A a treating catheter or a guide wire 403. Therefore, during a diagnosis, the probe 401 can be inserted exactly into a target point to be diagnosed while each part is monitored forward in the insertion direction A on the display unit 409 by passing the guide wire 403 through the guide unit 404. Likewise, during a treatment, a treating catheter is inserted through the guide unit 404 instead of the guide wire 403 to correctly treat a target part to be medically treated while it is visually monitored.

Figure 7:
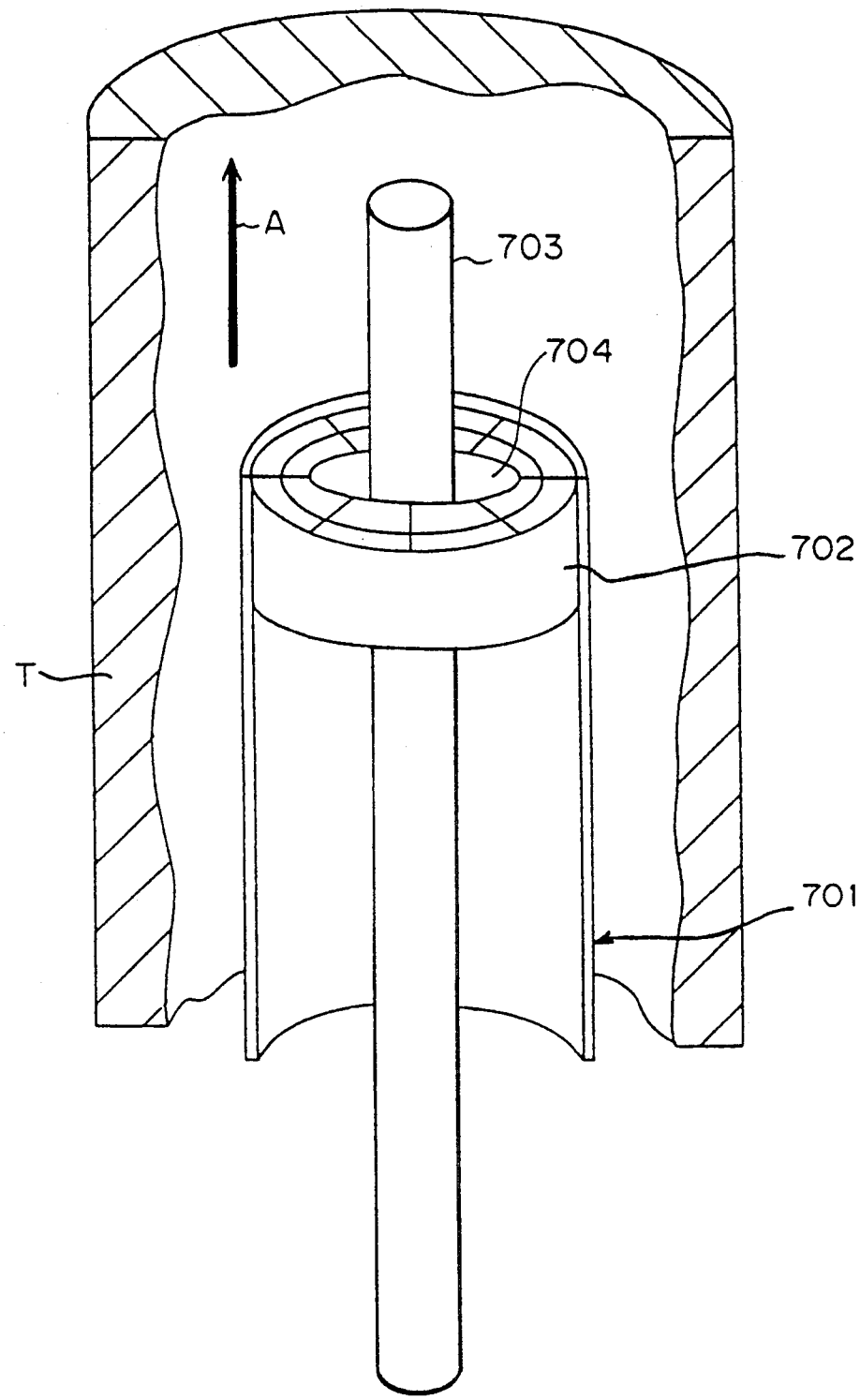
FIG. 7 is an oblique view illustrating the configuration of the ultrasonic probe used in the second embodiment of the present invention.

Next, FIG. 7 shows an ultrasonic probe 701 applied to the second embodiment of the present invention. A piezoelectric transducer 702 used in the probe 701 is divided into sixteen segments by circularly halving each of the eight segments of the ring-shaped piezoelectric transducer 402 shown in FIG. 5. Like in the first embodiment, the central part of the piezoelectric transducer 701 comprises a guide unit 704 for passing a guide wire 703 and a treating catheter. By equally dividing a piezoelectric transducer into sixteen parts, the piezoelectric transducer 702 has a larger capacity of wave data than the piezoelectric transducer 402 shown in FIG. 5, thereby providing a three-dimensional image containing a larger volume of information. Besides, it is obvious that a three-dimensional image having a larger volume of information can be obtained by dividing the piezoelectric transducer into a larger number of further smaller fan-shaped parts.

Figure 8:
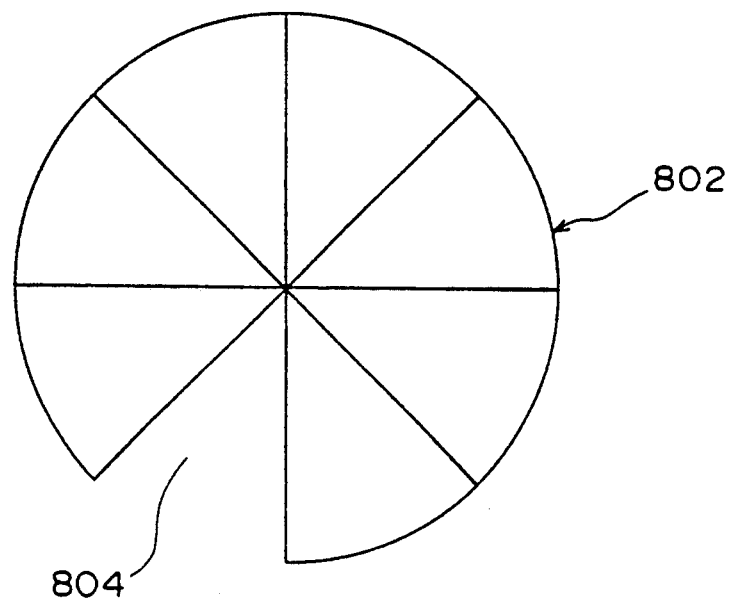
FIG. 8 is a plan view for explaining the configuration of the ultrasonic probe used in the third embodiment of the present invention.

FIG. 8 shows the configuration of a piezoelectric transducer 802 used in the ultrasonic probe applied to the third embodiment of the present invention. The saucer-shaped piezoelectric transducer 802 is divided radially into a plurality of sections (into eight parts in FIG. 8) and one section among them is removed. The space serves as a guide unit 804. This configuration provides almost the same effect as the first embodiment. In this embodiment, the piezoelectric transducer 802 can be divided radially and circularly into a larger number of further smaller segments.

Figure 9:
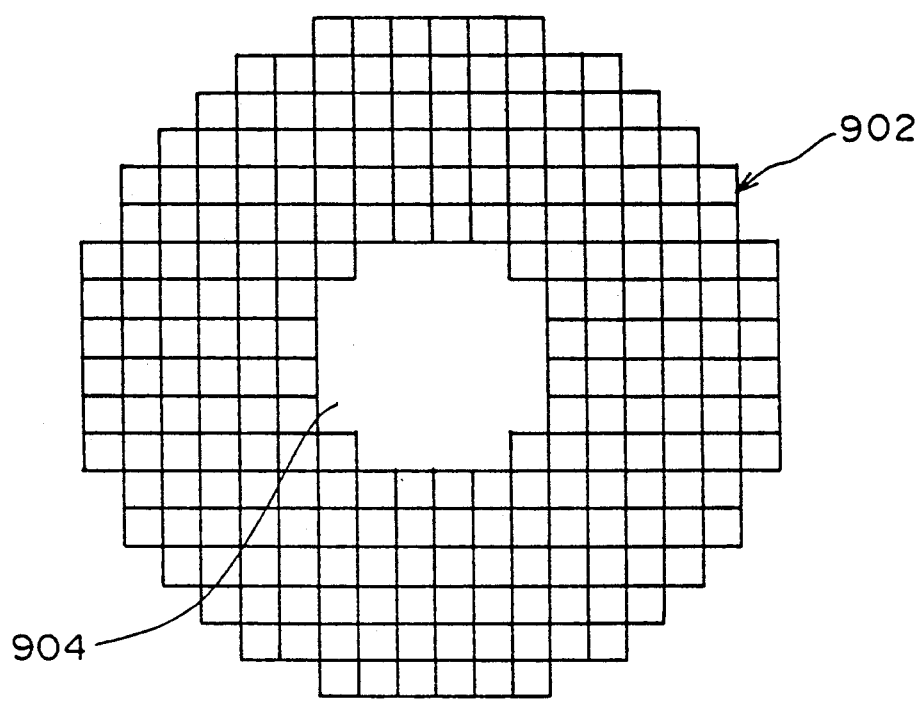
FIG. 9 is a plan view for explaining the configuration of the ultrasonic probe used in the fourth embodiment of the present invention.

FIG. 9 shows the configuration of a piezoelectric transducer 902 used in the ultrasonic probe applied to the fourth embodiment of the present invention. The piezoelectric transducer 902 comprises a number of fine sections obtained by dividing a ring-shaped piezoelectric transducer in a matrix format. Its central part serves as a guide unit 904. This embodiment can provide a larger volume of wave data than any other embodiments and generate a more detailed and precise three-dimensional image.

Each of the above described embodiments comprises a probe provided with a ring-shaped or a saucer-shaped piezoelectric transducer divided into a plurality of segments. However, the present invention is not limited to these applications and can be realized in other forms as long as a space in it serves as a guide unit.

Additionally, different kinds of treating catheters can be inserted at a time through guide units by providing in a probe a plurality of guide units.

The present invention easily generates a three-dimensional image of a part of an object to be medically diagnosed or treated forward of a probe in its insertion direction. The probe can be inserted exactly up to a part of an object to be medically diagnosed or treated while it is visually monitored through its three-dimensional image. As a result, a target part to be medically and ultrasonically diagnosed or treated can be recognized easily, thereby realizing a safe and precise medical treatment. It is obvious that the present invention can easily provide a conventional B mode or C mode image.

What is claimed is:

1. A catheter-type ultrasonic probe adapted to be inserted into a capillary, comprising:

a plurality of piezoelectric transducer segments provided at said probe for generating ultrasonic waves, and arrayed on a two-dimensional plane perpendicular or approximately perpendicular to an insertion direction in which said probe is inserted into the capillary with an ultrasonic wave emitting surface of said piezoelectric transducer segments facing in said insertion direction, only one of said piezoelectric transducer segments is used as an ultrasonic wave sending element, and the other ones of said piezoelectric transducer segments are used as reflected ultrasonic wave receiving elements; and guide means, in which none of said piezoelectric transducer segments exists, for passing a catheter or a guide wire through said piezoelectric transducer segments in said insertion direction.

2. A catheter-type ultrasonic probe according to claim 1, wherein
said piezoelectric transducer segments are arrayed to form a ring, and the central part serves as said guide means.

3. A catheter-type ultrasonic probe according to claim 2, wherein
said piezoelectric transducer segments are defined by a ring-shaped piezoelectric transducer radially divided into a plurality of segments.

4. A catheter-type ultrasonic probe according to claim 2, wherein
said piezoelectric transducer segments are defined by a ring-shaped piezoelectric transducer radially divided into a plurality of segments, and each of said segments being further divided into a plurality of subsegments.

5. A catheter-type ultrasonic probe according to claim 2, wherein
said piezoelectric transducer segments are defined by a ring-shaped piezoelectric transducer divided in a matrix format.

6. A catheter-type ultrasonic probe according to claim 1, wherein
said piezoelectric transducer segments are defined by a saucer-shaped piezoelectric transducer radially divided into a plurality of segments and having at least a portion of one of said segments removed to define said guide means.

7. An ultrasonic apparatus, comprising:
a catheter-type ultrasonic probe for insertion into a capillary, said probe including
a plurality of piezoelectric transducer segments provided at said probe for generating ultrasonic waves, and arrayed on a two-dimensional plane perpendicular or approximately perpendicular to an insertion direction in which said probe is inserted into the capillary with an ultrasonic wave emitting surface of said piezoelectric transducer segments facing in said insertion direction, only one of said piezoelectric transducer segments is used as an ultrasonic wave sending element, and the other ones of said piezoelectric transducer segments are used as reflected ultrasonic wave receiving elements, and guide means, in which none of said piezoelectric transducer segments exists, for passing a catheter or a guide wire through said piezoelectric transducer segments in said insertion direction; and imaging means for receiving output signals from said receiving elements, said output signals being based on ultrasonic waves emitted by said sending element and reflected at a measurement point, and for generating a three-dimensional image according to said output signals.

8. An ultrasonic apparatus according to claim 7, wherein said imaging means including:
driver means for driving said sending element to generate an ultrasonic wave impulse;

A/D converter means for converting each of said output signals of a plurality of said receiving elements to a digital signal;

wave memory means for storing according to each of the digital signals outputted by said A/D converter means, wave data indicating the transmission time in which an ultrasonic wave is generated by said sending element, reflected at a measurement point, and received by each of said receiving elements;

operating circuit means for identifying a measurement point corresponding to each piece of said wave data by comparing said wave data at each measurement point stored in said wave memory means with a prepared data mask indicating the relationship between a measurement point and the ultrasonic wave transmission time, and for generating three-dimensional image data according to the measurement point identification result; and display means for displaying said three-dimensional image data obtained by said operating circuit means.

* * * * *